United States Patent [19]

Lu et al.

[11] Patent Number: 5,652,144

[45] Date of Patent: Jul. 29, 1997

[54] YC1 GENE

[75] Inventors: Yinchen Lu, Wellesley; William A. Haseltine, Cambridge, both of Mass.

[73] Assignee: Dana-Farber Cancer Institute, Boston, Mass.

[21] Appl. No.: 973,431

[22] Filed: Nov. 10, 1992

[51] Int. Cl.$^6$ .......................... C12N 15/63; C12N 15/12
[52] U.S. Cl. .................. 435/320.1; 536/23.5; 536/23.1
[58] Field of Search .................... 536/23.5; 435/320.1

[56] References Cited

PUBLICATIONS

Steimer, et al., *Science*, vol. 254:105–108 (1991).
Strebel, et al., *Science*, vol. 241:1221–1223 (1988).
Allen, et al., *Science*, vol. 228:1091–1093 (1985).
Haseltine W., et al., *Raven Press* (1990).
Cohen, et al., *Journal of Acquired Immune Def. Syndromes*, vol. 3:11–18 (1990).
Rosen, et al., *Cell*, vol. 41:813–823 (1985).
Barre-Sinoussi, et al., *Science*, vol. 220:868–871 (1983).
Gallo, et al., *Science*, vol. 224:500–503 (1984).
Arya, et al., *Science*, vol. 229:69–73 (1985).
Sodroski, et al., *Science*, vol. 229:74–77 (1985).
Dayton, et al., *Cell.*, vol. 44:941–947 (1986).
Sodroski, et al., *Nature*, vol. 321:412–417 (1986).
Sodroski, et al., *Science*, vol. 231:1549–1553 (1986).
Cohen, et al., *Nature*, vol. 334:532–534 (1988).
Robey, et al., *Science*, vol. 228:593–595 (1985).
Klatzmann, et al., *Nature*, vol. 312:767–768 (1984).
Dalgleish, et al., *Nature*, vol. 312:763–767 (1984).
Lifson, et al., *Nature*, vol. 323:725–728 (1986).
Linsley, et al., *J. Virol.*, vol. 62:3695–3702 (1988).
Smith, et al., *Proc. Natl. Acad. Sci.*, vol. 86:8526–8530 (1989).
Ohno, T., et al., *Proc. Natl. Acad. Sci. U.S.A.*, vol. 88:10726–10729, (1991).
Matthews, T., et al., *Proc. Natl. Acad. Sci. U.S.A.*, vol. 83:9709–9713, (1986).
Javaherian, K., et al., *Science*, vol. 250:1590–1593, (1990).
Berman, P., et al., *Nature*, vol. 345:622–625, (1990).
Emini, E., et al., *Nature*, vol. 355:728–730, (1992).
Weiss, R.A., et al., *Nature*, vol. 324:572–575, (1986).

Profy, A., et al., *J. Immunol.*, vol. 144:4641–4647, (1990).
Ho, D., et al., *J. Virol.*, vol. 65:489–493, (1991).
Nara, P., et al., *J.Virol.*, vol. 64:3779–3791, (1990).
Gegerfelt, A., et al., *Virology*, vol. 185:162–168, (1991).
Arendrup, M., et al., *JAIDS*, vol. 5:303–307, (1992).
Lu, T., et al., *J.Virol.*, vol. 63:4115–4119, (1989).
Siekevitz, M., et al., *Science*, vol. 238:1575–1578, (1987).
Emerman M., et al., *Cell*, vol. 57:1155–1165, (1989).
Malim M., et al., *Nature*, vol. 338:254–257, (1989).
Fisher, A.G., et al., *Nature*, vol. 320:367–371, (1986).
Fisher, A.G., et al., *Science*, vol. 237:888–893, (1987).
Strebel, K., et al., *Nature*, vol. 328;728–730, (1987).
Kestler H.W., et al., *Cell*, vol. 65:651–662, (1991).
Yu, X–F, et al., *J. Virol.*, vol. 64:5688–5693, (1990).
Henderson, L.E., et al., *Science*, vol. 241:199–201, (1988).
Hu, W., et al., *Virology*, vol. 173:624–630, (1989).
Kappes, J.C., et al., *Virology*, vol. 184:197–209, (1991).
Hattori, N., et al., *Proc. Natl. Acad. Sci. U.S.A.*, vol. 87:8080–8084, (1990).
Terwilliger, E.F., et al., *Proc. Natl. Acad. Sci. U.S.A.*, vol. 86:5163–5167, (1989).
Klimkait, T., et al., *J. Virol.*, vol. 64:621–629, (1990).
Strebel, K., et al., *J. Virol*, vol. 63:3784–3791, (1989).
Willey, R., et al., *J.Virol*, vol. 66:226–234, (1992).
Helseth, E., et al., *J. Virol.* vol. 64:2416–2420, (1990).
Sodroski, J., et al., *Nature*, vol. 322:470–474, (1986).
Kowalski, K., et al., *J. Virol.*, vol. 65:281–291, (1991).
Leonard, C., et al., *J. Biol. Chem.*, vol. 265:10373–10382, (1990).
Skinner, M., et al., *J. Virol.*, vol. 62:4195–4200, (1988).
Kang, et al., *Proc. Natl. Acad. Sci.*, vol. 88:6171–6175 (1991).
Lu, et al., *J.Virol.*, vol. 64:5226–5229, (1990).
Calvert et al. Gene 101 (1991) pp. 171–176.
Garcia et al. Embo 1987 vol. 6(12) pp. 3761–3770.

*Primary Examiner*—David Guzo
*Attorney, Agent, or Firm*—David G. Conlin; Ronald I. Eisenstein

[57] ABSTRACT

Isolated and purified YC1 genes and proteins are disclosed. The protein binds to a site in the HIV-LTR, the NRE-1 site, and can inhibit the expression of a gene operably linked to the HIV-1 LTR. The use of the protein and gene are discussed. Repressible and inducible expression systems using the YC1 gene are also disclosed.

4 Claims, 8 Drawing Sheets

| Ad-2 ML USF site | G G C C A C G T G A C C |
|---|---|
| |        \| \| \| \| \| \| \| \| |
| HIV-1 NRE-1 | A G C A T T T C A T C A C T G G C |
| |        \| \| \| \| \| \| \| \| |
| IL-2 R-alpha | T T C A T C C C A G G |

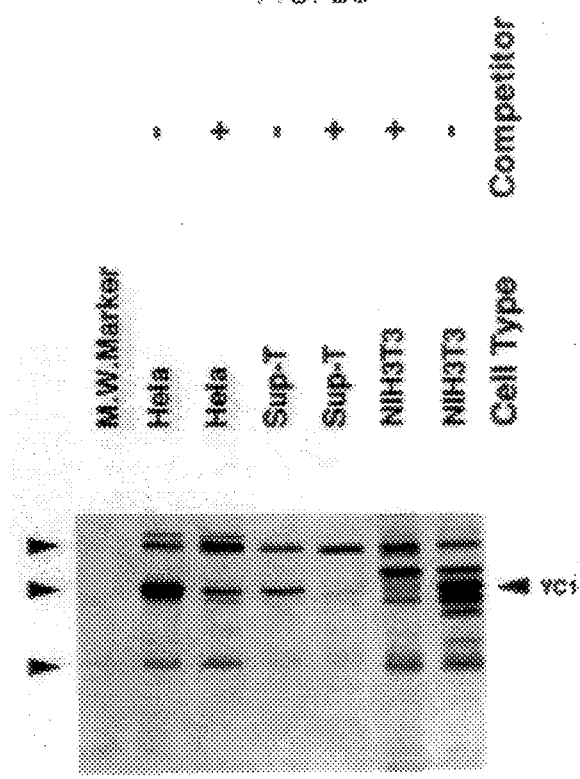

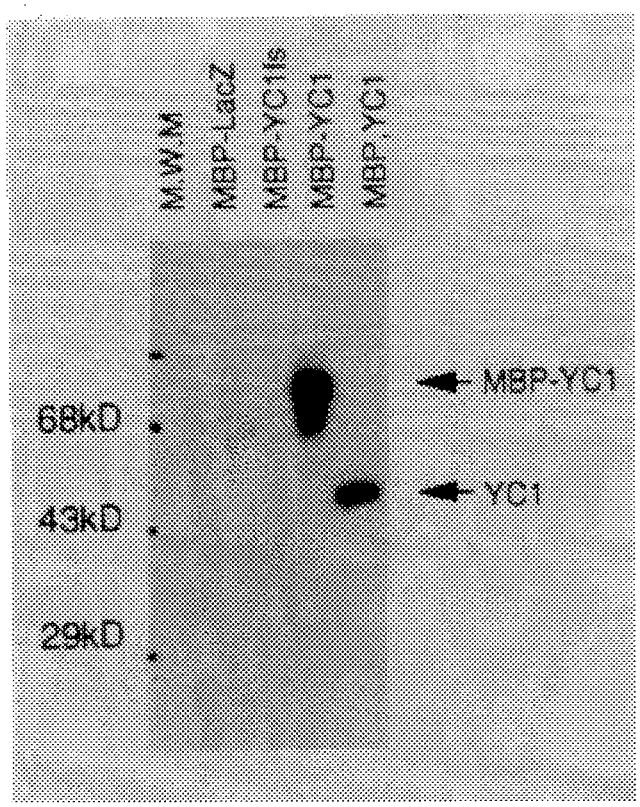
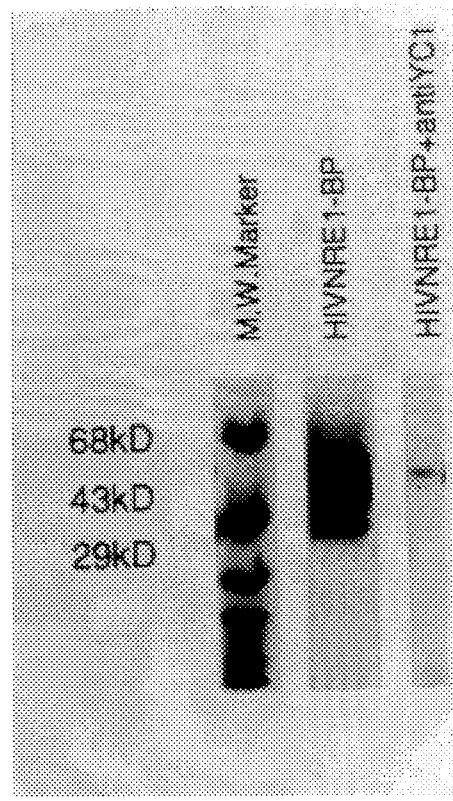

YC1 GENE

The present invention is directed to an isolated YC1 gene, an isolated and purified YC1 protein, probes therefore, and the use of such gene, protein and probes.

Human immunodeficiency virus type 1 (HIV-1) and, to a lesser extent, human immunodeficiency virus type 2 (HIV-2) are etiologic agents of acquired immune deficiency syndrome (AIDS) in humans [Barre-Sinoussi, F., et al., *Science* 220:868–871 (1983); Gallo R. C., et al., *Science* 224:500–503 (1984); Clavel, F., et al., *AIDS* 1:135–140 (1987)]. These viruses are related to simian immunodeficiency viruses that infect feral populations of sooty mangabeys, African green monkeys, and mandrills [Desrosiers, R. C., et al., *Ann. Rev. Immunol.* 8:557–558 (1990)].

These immunodeficiency viruses establish persistent infections in their hosts even in the face of an antiviral immune response. Part of this ability may reside in the capacity of these viruses to tightly regulate expression of the vital proteins, as evidenced by the presence of four conserved regulatory genes in all members of this group of retroviruses.

In addition to the gag, pro, pol and env genes typical of retroviruses, these viruses contain vif, tat, rev, and nef genes [Haseltine W., et al., *Raven Press* (1990)]. The tat protein stimulates the viral LTR to express viral RNA [Arya S., et al., *Science* 229:69–73 (1985); Sodroski J., et al., *Science* 229:74–77 (1985)] while the rev protein promotes the nuclear egress of viral messenger RNA's encoding the structural gene products [Emerman M., et al., *Cell* 57:1155–1165 (1989); Malim M., et al., *Nature* 338:254–257 (1989)]. Both tat and rev genes are essential for viral replication [Dayton A., et al., *Cell* 44:941–947 (1986); Fisher A. G., et al., *Nature* 320:367–371 (1986); Sodroski J., et al., *Nature* 321:412–417 (1986)]. The vif and nef genes, although dispensable for virus replication in some tissue culture settings, are well-conserved [Sodroski J., et al., *Science* 231:1549–1553 (1986); Fisher A. G., et al., *Science* 237:888–893 (1987); Strebel K., et al., *Nature* 328:728–730 (1987); Kestler H. W., et al., *Cell* 65:651–662 (1991)]. Depending upon the particular primate immunodeficiency virus, vpx, vpr and/or vpu genes are present in the proviral DNA [Desrosier R. C., et al., *Ann. Rev. Immunol.* 8: 557–578 (1990); Haseltine W., *Raven Press* (1990)]. These genes are also dispensable for virus replication in tissue culture. The vpx and vpr proteins are incorporated into virions and are believed to play a positive role in the early phase of the virus life cycle [Cohen E. A., et al., *JAIDS* 3:11–18 (1990); Yu, X.-F., et al., *J. Virol.* 64:5688–5693 (1990); Henderson L. E., et al., *Science* 241:199–201 (1988); Hu, W., et al., *Virology* 73:624–630 (1989); Kappes J. C., et al., *Virology* 184:197–209 (1991); Hattori N., et al., *Proc. Natl. Acad. Sci. U.S.A.* 87:8080–8084 (1990)]. The vpu gene is found only in HIV-1 and encodes a 15–20 kD protein, depending upon the virus isolate [Terwilliger E. F., et al., *Proc. Natl. Acad. Sci. U.S.A.* 86:5163–5167 (1989); Cohen E. A., et al., *Nature* 344:532–534 (1988); Strebel K., et al., *Science* 241:1221–1223; (1988); Klimkait T., et al., *J. Virol.* 64:621–629 (1990)]. The vpu protein is associated with the host cell membranes and facilitates the redistribution of viral proteins from inside the infected cell to free virion particles [Terwilliger E. F., et al., *Proc. Natl. Acad. Sci. U.S.A.* 86:5163–5167 (1989); Cohen E. A., et al., *Nature* 344:532–534 (1988); Strebel K., et al., *Science* 241:1221–1223; (1988); Klimkait T., et al., *J. Virol.* 64:621–629 (1990); Strebel K., et al, *J. Virol.* 63:3784–3791 (1989)]. Thus, the major function of the vpu product is to modulate virus release, although other effects of vpu on envelope glycoprotein or CD4 steady state levels have been observed [Willey R., et al., *J. Virol.* 66:226–234 (1992); Kimura T. and Karn J., personal communication].

The persistence of primate immunodeficiency virus infection is also made possible by the particular features of the viral envelope glycoproteins. The viral glycoproteins are synthesized as a 160 Kd precursor, which is cleaved intracellularly to yield the gp120 exterior envelope glycoprotein and the gp41 transmembrane glycoprotein [Allan J. S., et al., *Science* 228:1091–1093 (1985); Robey W. G., et al., *Science* 228:593–595 (1985)]. The gp120 glycoprotein binds the CD4 receptor, following which the gp120 and gp41 glycoproteins in concert contribute to the membrane fusion process [Klatzmann D., et al., *Nature* 312:767–768 (1984); Dalgleish A. G., et al., *Nature* 312:763–767 (1984); Helseth E., et al., *J. Virol.* 64:2416–2420 (1990)]. The latter process mediates both virus entry and viral cytopathic effect, which consists of multinucleated giant cell (syncytium) formation and single cell lysts [Sodroski J., et al., *Nature* 322:470–474 (1986); Lifson J. D., et al., *Nature* 323:725–728 (1986); Kowalski K., et al., *J. Virol.* 65:281–291 (1991)]. The exterior envelope glycoproteins of these viruses are heavily glycosylated and contain regions of hyper-variability, most of which are thought to consist of disulfide-linked loops exposed to the exterior of the protein [Leonard C., et al., *J. Biol. them.* 265:10373–10382 (1990)]. In the case of HIV-1, most of the neutralizing antibody response elicited early in the course of infection is directed against the third variable (V3) loop of the gp120 glycoprotein [Nara P., et al., *Proc. Quatreime Colloque des Cent Gardes* (Girard, Valette, eds, Paris: Pasteur Vaccins) pp. 203–215 (1989)]. These antibodies inhibit some aspect of the membrane fusion process [Skinner M., et al., *J. Virol.* 62:4195–4200 (1988); Linsley P., et al., *J. Virol.* 62:3695–3702 (1988)]. Neutralization is generally strain-restricted due to variation in the V3 region, but some antibodies recognize better conserved elements near the tip of the loop [Ohno T., et al., *Proc. Natl. Acad. Sci. U.S.A.* 88:10726–10729 (1991); Matthews T., et al., *Proc. Natl. Acad. Sci. U.S.A.* 83:9709–9713 (1986); Javaherian K., et al., *Science* 250:1590–1593 (1990)]. The anti-V3 loop antibodies are protective against intravenous challenge by homologous HIV-1 [Berman P., et al., *Nature* 345:622–625 (1990); Emini E., et al., *Nature* 355:728–730 (1992)]. Later in the course of HIV-1 infection, antibodies that neutralize a broader range of HIV-1 isolates are generated [Weiss R. A., et al., *Nature* 324:572–575 (1986); Profy A., et al., *J. Immunol.* 144:4641–4647 (1990); Berkower I., et al., *J. Exp. Med.* 170:1681–1695 (1989)]. These antibodies recognize discontinuous epitopes near the CD4 binding site of gp120 and block the binding of gp120 to CD4 [Ho D., et al., *J. Virol.* 65:489–493 (1991); Kang C.-Y., et al., *Proc. Natl. Acad. Sci. U.S.A.* 88:6171–6175 (1991); Stetmer K. S., et al., *Science* 254:105–108 (1991)]. These neutralizing antibodies do not keep virus replication in check indefinitely, probably because of virus variation and selection of neutralization-resistant viruses and because of immunosuppression and compromised ability of the host to respond to novel epitopes [Nara P., et al., *J. Virol.* 64:3779–3791 (1990); Gegerfelt A., et al., *Virology* 185:162–168 (1991); Arendrup M., et al., *JAIDS* 5:303–307 (1992)].

The LTRs of the primate immunodeficiency viruses contain cis-acting regulatory elements which also regulate viral protein expression [Rosen, C. A., et al., *Cell* 41:813–823 (1985)]. The LTR contains enhancer elements, promoter elements, the tar region, which results in greatly increased levels of HIV LTR directed gene expression and the NRE region, which is a region that negatively regulates gene expression directed by HIV LTRs. There appears to be an intricate interplay in viral state as a result of these different regulatory sequences.

In the normal course of disease progression, the virus after its initial infection remains in a latent state, which can last up to about 10 years, before there's a transformation in the virus resulting in many of the symptoms associated with immunodeficiency diseases, such as persistent generalized lymphadenopathy syndrome (PGL), AIDS related complex (ARC) and AIDS.

It would be useful to have a marker that could be used to determine the stage the virus is at to help monitor when such a transition is likely to occur.

It would be useful to have a compound which can effect expression of genes operably linked to other promoters.

It would also be useful to have a compound which can negatively effect protein expression of a gene operably linked to a vital promoter such as the HIV LTR. This could permit methods of screening for inhibitory compounds, methods of therapy and methods of modifications of compounds.

SUMMARY OF INVENTION

We have now found and isolated a gene and a protein expressed by that gene, which specifically binds to a region within the NRE of the HIV LTR. This protein can negatively effect expression directed by the HIV LTR in vitro. The protein referred to as YC1 is 406 amino acids (SEQ ID NO:1):

| 1 | Met | gly | lys | val | trp | lys | gln | gln | met | tyr | pro | gln | tyr | ala | thr |
|---|---|---|---|---|---|---|---|---|---|---|---|---|---|---|---|
| 16 | Tyr | tyr | tyr | pro | gln | tyr | leu | gln | ala | lys | gln | ser | leu | val | pro |
| 31 | ala | his | pro | met | ala | pro | pro | ser | pro | ser | thr | thr | ser | ser | asn |
| 46 | asn | asn | ser | ser | ser | ser | ser | asn | ser | gly | trp | asp | gln | leu | ser |
| 61 | asn | ala | asn | leu | tyr | ile | arg | gly | leu | pro | pro | his | thr | thr | asp |
| 76 | gln | asp | leu | val | lys | leu | cys | gln | pro | tyr | gly | lys | ile | val | ser |
| 91 | thr | lys | ala | ile | leu | asp | lys | thr | thr | asn | lys | cys | lys | gly | tyr |
| 106 | gly | phe | val | asp | phe | asp | ser | pro | ala | ala | ala | gln | lys | ala | val |
| 121 | ser | ala | leu | lys | ala | ser | gly | val | gln | ala | gln | met | ala | lys | gln |
| 136 | gln | glu | gln | asp | pro | thr | asn | leu | tyr | ile | ser | asn | leu | pro | leu |
| 151 | ser | met | asp | glu | gln | glu | leu | glu | asn | met | leu | lys | pro | phe | gly |
| 166 | gln | val | ile | ser | thr | arg | ile | leu | arg | asp | ser | ser | pro | thr | ser |
| 181 | arg | gly | val | gly | phe | ala | arg | met | glu | ser | thr | glu | lys | cys | glu |
| 196 | ala | val | ile | gly | his | phe | asn | gly | lys | phe | ile | lys | thr | pro | pro |
| 211 | gly | val | ser | ala | pro | thr | glu | pro | leu | leu | cys | lys | phe | ala | asp |
| 226 | gly | gly | gln | lys | lys | arg | gln | asn | pro | asn | lys | tyr | ile | pro | asn |
| 241 | gly | arg | pro | trp | his | arg | glu | gly | glu | val | arg | leu | ala | gly | met |
| 256 | thr | leu | thr | tyr | asp | pro | thr | thr | ala | ala | ile | gln | asn | gly | phe |
| 271 | tyr | pro | ser | pro | tyr | ser | ile | ala | thr | asn | arg | met | ile | thr | gln |
| 286 | thr | ser | ile | thr | pro | tyr | ile | ala | swer | pro | val | ser | ala | tyr | gln |
| 301 | val | gln | ser | pro | ser | trp | met | gln | pro | gln | pro | tyr | ile | leu | his |
| 316 | asp | pro | gly | ala | val | leu | thr | pro | ser | met | glu | his | thr | met | ser |
| 331 | leu | gln | pro | ala | ser | met | ile | ser | pro | leu | ala | gln | gln | met | ser |
| 346 | his | leu | ser | leu | gly | ser | thr | gly | thr | tyr | met | pro | ala | thr | ser |
| 361 | ala | met | gln | gly | ala | tyr | leu | pro | glu | tyr | ala | his | met | gln | thr |
| 376 | thr | ala | val | pro | val | glu | glu | ala | ser | gly | gin | gln | gln | val | ala |
| 391 | val | glu | thr | ser | asn | asp | his | ser | pro | tyr | thr | phe | gln | pro | asn |
| 406 | lys | *** | | | | | | | | | | | | | |

The cDNA for this protein is 1534 muchleotides in length and has SEQ ID NO:2.

1
GA ATT CGG GCC GAG ACT TGG AAA CCC CAA AGT GTC CGC GAC CCT G

46
CA CGG CAG CTC CCT TCC AGC TTC ATG GGC AAA GTG TGG AAA CAG C

91
AG ATG TAC CCT CAG TAC GCC ACC TAC TAT TAC CCC CAG TAT CTG C

136
AA GCC AAG CAG TCT CTG GTC CCA GCC CAC CCC ATG GCC CCT CCC A

181
GT CCC AGC ACC ACC AGC AGT AAT AAC AAC AGT AGC AGC AGT AGC A

226
AC TCA GGA TGG GAT CAG CTC AGC AAA ACG AAC CTC TAT ATC CGA G

271
GA CTG CCT CCC CAC ACC ACC GAC CAG GAC CTG GTG AAG CTC TGT C

-continued

```
316
AA CCA TAT GGG AAA ATA GTC TCC ACA AAG GCA ATT TTG GAT AAG A

361
CA ACG AAC AAA TGC AAA GGT TAT GGT TTT GTC GAC TTT GAC AGC C

406
CT GCA GCA GCT CAA AAA GCT GTG TCT GCC CTG AAG GCC AGT GGG G

451
TT CAA GCT CAA ATG GCA AAG CAA CAG GAA CAA GAT CCT ACC AAC C

496
TC TAC ATT TCT AAT TTG CCA CTC TCC ATG GAT GAG CAA GAA CTA G

541
AA AAT ATG CTC AAA CCA TTT GGA CAA GTT ATT TCT ACA AGG ATA C

586
TA CGT GAT TCC AGT CCT ACA AGT CGT GGT GTT GGC TTT GCT AGG A

631
TG GAA TCA ACA GAA AAA TGT GAA GCT GTT ATT GGT CAT TTT AAT G

676
GA AAA TTT ATT AAG ACA CCA CCA GGA GTT TCT GCC CCC ACA GAA C

721
CT TTA TTG TGT AAG TTT GCT GAT GGA GGA CAG AAA AAG AGA CAG A

766
AC CCA AAC AAA TAC ATC CCT AAT GGA AGA CCA TGG CAT AGA GAA G

811
GA GAG GTG AGA CTT GCT GGA ATG ACA CTT ACT TAC GAC CCA ACT A

856
CA GCT GCT ATA CAG AAC GGA TTT TAT CCT TCA CCA TAC AGT ATT G

901
CT ACA AAC CGA ATG ATC ACT CAA ACT TCT ATT ACA CCC TAT ATT G

946
CA TCT CCT GTA TCT GCC TAC CAG GTG CAA AGT CCT TCG TGG ATG C

991
AA CCT CAA CCA TAT ATT CTA CAC GAC CCT GGT GCC GTG TTA ACT C

1036
CC TCA ATG GAG CAC ACC ATG TCA CTA CAG CCC GCA TCA ATG ATC A

1081
GC CCT CTG GCC CAG CAG ATG AGT CAT CTG TCA CTA GGC AGC ACC G

1126
GA ACA TAC ATG CCT GCA ACG TCA GCT ATG CAA GGA GCC TAC TTG C

1171
CA CAG TAT GCA CAT ATG CAG ACG ACA GCG GTT CCT GTT GAG GAG G

1216
CA AGT GGT CAA CAG CAG GTG GCT GTC GAG ACG TCT AAT GAC CAT T

1261
CT CCA TAT ACC TTT CAA CCT AAT AAG TAA CTG TGA GAT GTA CAG A

1306
AA GGT GTT CTT ACA TGA AGA AGG GTG TGA AGG CTG AAC AAT CAT G

1351
GA TTT TTC TGA TCA ATT GTG CTT TAG GAA ATT ATT GAC AGT TTT G

1396
CA CAG GTT CTT GAA AAC GTT ATT TAT AAT GAA ATC AAC TAA AAC T

1441
AT TTT TGC TAT AAG TTC TAT AAG GTG CAT AAA ACC CTT AAA TTC A

1486
TC TAG TAG CTG TTC CCC CGA ACA GGT TTA TTT TAG TAA AAA AAA A

1531
AA AA
```

BRIEF DESCRIPTION OF THE FIGURES

FIG. 2C shows that the YC1 antiserum specifically recognizes the authentic YC1 protein in different mammalian cells.

FIG. 3A shows a Western blot analysis of MBP-LacZ, MBP-YC1fs, MBP-YC1, MBP and YC1 using mouse anti-MBPYC1 serum.

FIG. 3B shows a Southwestern blot analysis of the same set of samples using $P^{32}$ labeled double stranded oligonucleotide derived from the HIV-1 NRE-1 site as a probe.

FIG. 3C shows immunoprecipitation of HIV-1 NRE-1 binding protein from HeLa cell nuclear extract by YC1 antisera.

DETAILED DESCRIPTION OF THE INVENTION

Figure 1B:
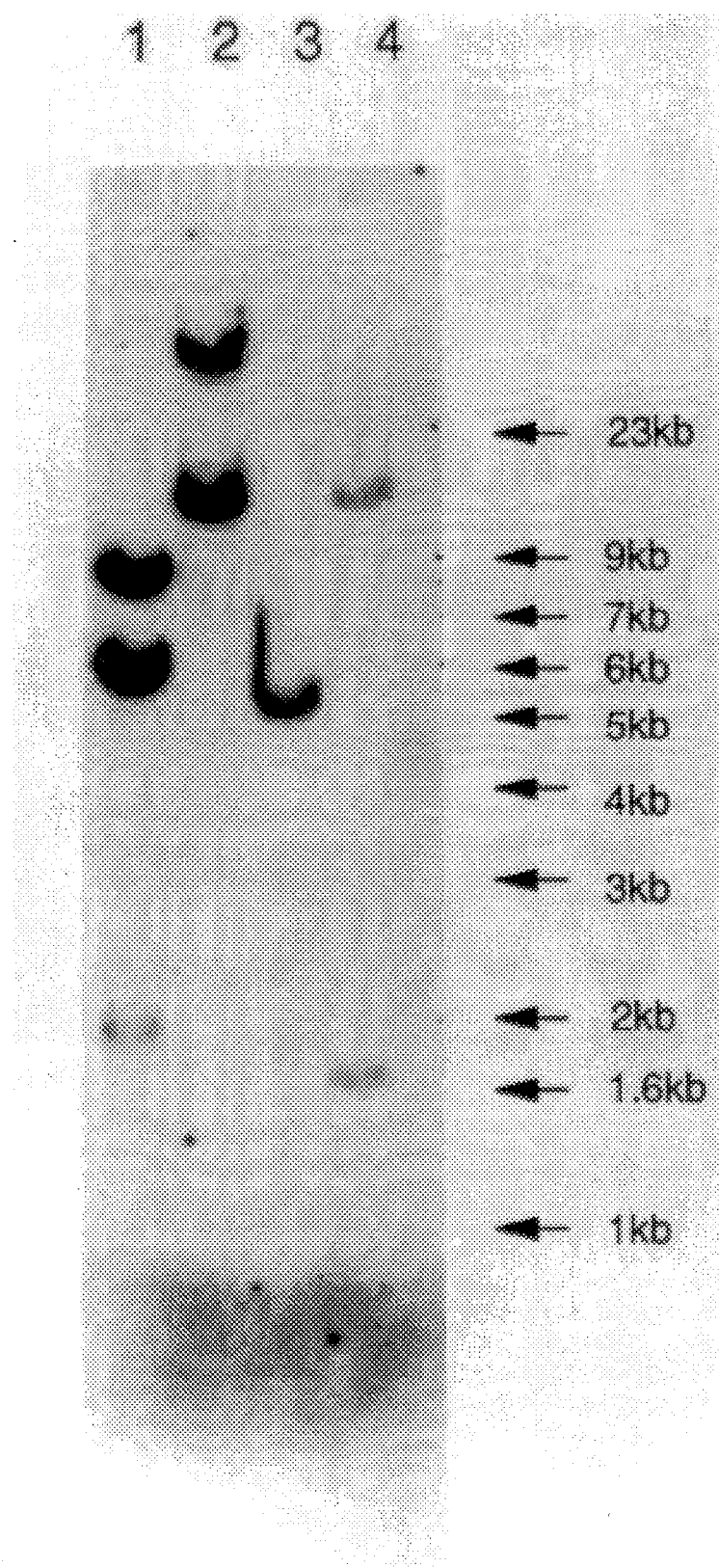
FIG. 1B shows a Southern blot analysis of YC1.

We have now discovered a protein that will bind specifically to a region within the negative regulatory element (NRE) of primate immunodeficiency viruses (sometimes referred to as HIV viruses), particularly HIV-1.

The various HIV viruses have a NRE sequence within the LTR. Whereas some of the sequences in the viral LTR enhance the rate of RNA synthesis, those within the NRE decrease LTR directed gene expression. [Lu, Y., et al., *J. Virol.* 64:5226–5229 (1990); Lu, Y., et al., *J. Virol.* 63:4115–4119 (1989); Rosen, et al., *Cell* 41, supra; Siekevitz, M., et al., *Science* 238:1575–1578 (1987)]. Specific regions within the NRE have been identified as contributing to the negative effect of the NRE on promoter activity and virus replication. For example, NRE-1, previously referred to as USF, which appears between sequences −159 and −173, and NRE-2, previously referred to as NFAT-1, which is located between nucleotides −253 and −213 [Lu, Y., et al., J. of Virol. 64, supra]. The sequences which contribute to these two regions have also been identified as having highly homologous regions in the sequence 5' to the site of RNA initiation of the IL-2 gene and IL-2 Ralpha-chain gene (IL-2Rα). The NRE-1 site in the IL-2 Rα-chain promoter has been demonstrated to be the site for a negative regulatory factor and the same factor also appears to bind to the homologous site in the HIV LTR. The NRE-2 site responds to T-cell activation signals by recognition of a transcription factor activated upon T-cell stimulation.

We have now isolated and purified a protein that binds to the NRE-1 site, which is referred to herein as YC1.

The gene encoding the YC1 protein (the YC1 gene) encodes a 406 amino acid long protein. The resultant protein is 47 kD (although its calculated molecular weight is 45 kD) and has (SEQ ID NO:1). See, also FIG. 1A.

The protein is rich in serine and threonine; which account for almost one-fifth of the total amino acids of the protein.

A serine rich domain is underlined in FIG. 1A. The protein contains two motifs previously associated with DNA binding activity, a leucine zipper-like motif located near the center (amino acids 143 to 161), and two putative helix-turn-helix in the center of the molecule (amino acids 112 to 164 and 187 to 226). The leucine residues that are part of the Leucine zipper are boxed in FIG. 1A.

This protein is isolated from the cell by standard techniques well known in the art. For example, centrifugation followed by gel filtration. This protein is frequently associated with nucleic acid and it is preferred that the protein is also substantially free of extraneous nucleic acid. Preferably, the isolated protein is substantially purified so that it has a purity of at least about 95%, more preferably, at least about 98%, still more preferably, at least about 99%.

Although the YC1 binding sequence, NRE-1 is similar to the USF-1 sequence, which was initially described as a regulatory element present in the adenovirus E1A promoter, the YC1 protein is not similar in sequence to the cellular protein that binds to the USF-1 sequence, the USF-1 protein. [Gregor, P., et al., *Gene & Development* 4:1730–1740 (1990). While the USF-1 binding protein has previously been shown to bind within the NRE-1 sequence of the HIV LTR, in in vitro extracts it does not repress transcription directed by the HIV-1 LTR. In contrast, the addition of the YC1 protein will negatively effect expression of a gene operably-linked to the HIV-1 LTR in in vitro extracts. This indicates that the USF-1 binding protein and the YC1 proteins, perform different functions in vivo. Smith, M. R., et al., *Proc. Natl. Acad. Sci.* 86:8526–8530 (1989) described a generally uncharacterized protein that is stated to be 50 kD, but such protein is bound to labeled DNA, and thus not isolated and purified.

Although the HIV viruses show significant nucleotide variation, and even within a given virus, significant strain to strain variation, there is a general functional sequence homology known to the skilled artisan. Thus, knowing the NRE-1 sequence of HIV-1 and the YC1 protein, the skilled artisan can readily use the YC1 protein against other members of the HIV family, for example, HIV-2 or SIV.

The YC1 protein is not a virally-produced protein, but is constitutively expressed by cells. It will also bind to sequences similar to the NRE-1 located near other promoters, such as the IL-2 Rα, wherein it will negatively effect expression. A central region of the NRE-1 sequence is similar to the NRE of the IL-2 Rα promoter. Accordingly, by having a sequence corresponding to the NRE-1 sequence operably linked to a promoter for a desired gene one can negatively regulate its expression by the addition of the YC1 protein. The NRE-1 sequence can be inserted by standard techniques well known to the skilled artisan. When the promoter sequence is a viral LTR the NRE-1 sequence can be inserted into the LTR. This can be done by standard techniques based upon the present disclosure. Preferably, the sequences which correspond to the NRE-1 sequences are inserted 5' to the positive regulatory elements. The YC1 protein can be used in a method for inhibiting the expression of a gene operably linked to an HIV-1 LTR by administering an inhibition effective amount of the protein of claim 1. Preferably, the gene is an HIV gene such as HIV-1 env, gag, tat, or rev, and the inhibition effective amount of the protein is at least about 3 times the constitutive amount of protein produced by the cell. More preferably, one uses an amount of protein that ranges from 0.1 mg to about 10 mg of protein/kg of body weight.

The HIV-1 LTR and IL-2Rα promoters both contain NF-κB binding site. For example, having the gene operably linked to the HIV-1 LTR or IL-2Rα promoter. Then you can repress expression by adding a sufficient amount of the YC1 protein or RNA. Expression dan be obtained by adding a sufficient amount of p65-p50. This dual expression system can be used to regulate expression of a wide variety of genes such as genes for proteins such as cytokines, lymphokines, hormones, growth factors, etc.

As used herein, the term YC1 protein refers to the full length protein, i.e. that comprising (SEQ ID NO:1), as well as a functional portion of this protein. For example, YC1A, which does not contain the first 33 amino acids of YC1 (the dotted underlined amino acids in FIG. 1A) is functional. Similarly, at least the first 100 amino acids are not needed to bind to the NRE-1 and inhibit HIV LTR directed expression. The remaining three-quarters of the protein are more important for such functional activity. For example, it is expected that the binding domain is located somewhere between amino acids 109 and 200. Although not wishing to be bound by theory it is believed that the C-terminal portion is the active site with respect to the function of inhibiting HIV LTR directed express. Thus, the functional portion of the YC1 protein does not have to contain at least the first 109 amino acids of the YC1 protein.

In addition, constitutive amino acid substitutions (i.e. substitutions, deletions, and additions) can be tolerated in the fucntional portion, whereas a wider degree of variation, is permitted in the first 109 amino acids, which are not necessary. Thus, such portion will tolerate virtually any deletion, addition or substitution, as long as it does not adversely interfere with the protein's binding ability and the functional portion of the carboxy-most part of the protein. Such changes can readily be determined empirically by the skilled artisan, based upon the present disclosure. For example, by using an in vitro transcription assay, wherein a gene, such as the CAT gene, is under the control of the HIV-1 LTR, the gene's expression can be compared with to a standard control, e.g., wherein the full-length YC1 protein has been added to such a CAT assay under the same amounts and conditions.

The present protein also permits a method for developing a mutein of the YC1 protein having enhanced negative regulatory abilities. For example, one can use the YC1 gene and by site-directed mutagenesis, preferably in the carboxy portion, one can prepare a whole range of YC1 muteins. One can then screen for a mutein having enhanced functional abilities by standard screening techniques, such as an in vitro transcription assay using the above HIV CAT assay, one can readily add the muteins to the assay to select the muteins having enhanced negative regulatory abilities.

The DNA segment corresponding to the YC1 gene (SEQ ID NO:2) can be used as part of an expression vector. For example, one can have such segment operably linked to a promoter. Preferably, the promoter is heterologous to the DNA segment. Promoters can readily be chosen by the skilled artisan depending upon the host cell you wish to use for expression of the protein.

In addition, because this protein is of cellular origin expressed and has been demonstrated to bind to the NRE-1 sequence and inhibit HIV LTR expression, a probe for YC1, its RNA or DNA can be used to evaluate changes in virulence of the virus. This type of screening can be done by a variety of means, for example, using a YC1 antibody, or by using PCR amplification for the DNA or RNA.

Antibodies to the YC1 protein that can be used in such assays can readily be made. For example, polyclonal, monoclonal, or bispecific antibodies can be generated by known techniques based upon the present disclosure.

The immune system can be used to prepare an antibody which will bind to the YC1 protein by standard immunological techniques. For example, using the protein or an immunogenic fragment thereof or a peptide chemically synthesized based upon such protein. Any of these sequences can be conjugated, if desired, to keyhole limpet hemocyanin (KLH) and used to raise an antibody in animals such as a mice, rabbits, rats, and hamsters. Thereafter, the animals are sacrificed and their spleens are obtained. Monoclonal antibodies are produced by using standard fusion techniques for forming hybridoma cells. See, Kohler, G., et al. *Nature* 256:495 (1975). This typically involves fusing an antibody-producing cell (i.e., spleen) with an immortal cell line such as a myeloma cell to produce the hybrid cell.

Another method for preparing antibodies is by in vitro immunization techniques, such as using spleen cells, e.g., a culture of murine spleen cells, injecting an antigen, and then screening for an antibody produced to said antigen. With this method, as little as 0.1 micrograms of antigen can be used, although about 1 microgram/mililiter is preferred. For in vitro immunization, spleen cells are harvested, for example, mice spleen cells, and incubated at the desired amount, for example, $1 \times 10^7$ cells/mililiter, in medium plus with the desired antigen at a concentration typically around 1 microgram/mililiter. Thereafter, one of several adjuvants depending upon the results of the filter immunoplaque assay are added to the cell culture. These adjuvants include N-acetylmuramyl-L-alanyl-D-isoglutamine [Boss, *Methods in Enzymology* 121:27–33 (1986)]. Salmonella typhimurium mytogen [Technical Bulletin, Ribi ImmunoChem. Res. Inc., Hamilton, Mont.] or T-cell condition which can be produced by conventional techniques [See, Borrebaeck, C. A. K., *Mol Immunol.* 21:841–845 (1984); Borrebaeck, C. A. K., *J. Immunol.* 136:3710–3715 (1986) or obtained commercially, for example, from Hannah Biologics, Inc. or Ribi ImmunoChem. Research Inc. The spleen cells are incubated with the antigen for four days and then harvested.

Single cell suspensions of the in vitro immunized mouse spleen cells are then incubated, for example on antigen-nitrocellulose membranes in microfilter plates, such as those available from Millipore, Corp.

The antibodies produced are detected by using a label for the antibodies such as horseradish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find antibodies of interest. Cultures containing the antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody.

This latter technique is preferred over in vivo immunization because the in vivo method typically requires about 50 micrograms of antigen per mouse per injection and there are usually two boosts following primary immunization for the in vivo method.

The presence of YC1 can be determined by assaying for it using the antibodies, or YC1 nucleic acid, e.g. DNA or RNA, as a probe. In one preferred embodiment, the probe would be an antibody, in for example, a quantitative immunoassay. By such methods, one can determine whether the level of YC1 has increased, decreased or remained unchanged. One can then compare results against a standard baseline level. For example, one can take samples from the same individual at various time to monitor continuing levels of expression. Alternatively, one can compare the level against a standard determined by screening multiple individuals. The YC1 protein and nucleic acid is detectable in a wide range of cells and body tissues. Most preferably, one would measure its expression in T-cells.

These antibodies can be used to determine the amount of YC1 in a sample by contacting the sample, e.g. cell or tissue, with at least one of the probes, e.g. an antibody, preferably, a monoclonal antibody, and determining whether binding has occurred. One can also use a nucleotide probe to determine the level of expression of such protein. When one is using a nucleotide probe, one preferably uses PCR technology. By monitoring the level of expression, one can determine disease state and also determine the most appropriate therapy to be used.

In accord herewith, the presently described antibody or a cocktail of probes including antibodies to other proteins that one wishes to monitor at the same time such as for a broadly neutralizing envelope glycoprotein can be used for detection. The antibody probes can be labeled directly with a reportor or indirectly with a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; bitoin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfdhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, detectably-labelled antibodies, or detectably-labelled member of the specific binding pair is coupled to a reporter which can be a radioactive isotope, enzyme, fluorogenic, chemiluminescent or electrochemical materials. Commonly used radioactive isotopes are $^{125}$I, $Tc^{99m}$ and $^{3}$H. Standard radioactive isotopic labeling procedures include the chloramine T, lactoperoxidase and Bolton-Hunter methods for $^{125}$I and reduction methylation for $^{3}$H.

Enzymes suitable for use in this invention include, but are not limited to, horseradish peroxidase, alkaline phosphatase, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, *Immunochemistry* 8:871 (1971), Avrameas and Ternynck, *Immunochemistry* 8:1175 (1975), Ishikawa et al., *J. Immunoassay* 4 (3):209–327 (1983) and Jablonski, *Anal. Biochem.* 148:199 (1985), which are incorporated by reference.

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support. Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

Although the YC1 protein is constutively expressed in vitally-infected cells, we believed that supplementing the amount of the protein in such cells can assist a cell to more successfully inhibit the expression of a gene operably-linked to a promoter containing such a sequence, such as the HIV LTR. Thus, the purified protein can be used therapeutically. Genes expressing YC1 can be preferentially brought to CD4 cells by using a monoclonal antibody as a carrier, for example, by the system of Wu, and Wu, *J. Biol Chem* 262:4429–4432 (1987).

One can also use any of the known forms of gene therapy to deliver the YC1 gene to CD4 positive lymphocytes. For example, using a cell-specific gene transfer mechanism, which uses receptor-mediated endocytosis to carry RNA or DNA molecules into cells (See, for example, Wu & Wu, *J. Biol. Chem.* 262, supra. A protein acting as a ligand is coupled to a poly-L-lysine, which then combines with RNA or DNA (the gene) or the YC1 protein to form soluble complexes by strong electrostatic interaction, whereby one can deliver the genes (i.e. the RNA or DNA) or the protein to the cells of interest such as CD4 cells. For example, using an antibody against gp120 or CD4 as the ligand, one can specifically target such cells. Indeed, such a method of in vivo gene transfer in addition to serving as a vector to deliver a therapeutic agent such as YC1 into HIV infected cells or cells susceptible of HIV infection, could also utilize the neutralizing activity of the antibody.

The gene or a protein can be attached to an antibody such as an antibody to CD4 receptors in the same manner as other labels resulting in a coupled conjugate.

The purified protein can be delivered by any of a number of means. For example, it can be administered by parenteral injection (intramuscular, I.M.), intraperitoneal (I.P.), intravenous (I.V.), or subcutaneous (S.C.), oral or other routes of administration well-known in the art. Parenteral administration is preferred.

The amount used will typically be in the range from about 0.1 mg to about 10 mg/kg of body weight. The protein will preferably be formulated in a unit dose.

For example, solid dose forms that can be used for oral administration include capsules, tablets, pills, powders and granules. In such solid dose forms, the active ingredient, i.e., antibody or peptide, is mixed with at least one inert carrier such as sucrose, lactose or starch. Such dose forms can also comprise additional substances other than inert diluents, e.g., lubricating agents, such as magnesium stearate.

Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody or protein. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

The present invention is further illustrated by the following examples. These examples are provided to and in the understanding of the invention and are not to be construed as a limitation thereof.

The protein that binds to the NRE-1 sequence was identified as follows.

A phage λgt11 cDNA library was screened as described by H. Singh, et al., *BioTechniques* 7:252 (1989). The cDNA library derived from the activated Jurkat cells was purchased from CLONETECH. The recombinated phage plaques were plated at a density of less than 10,000 plaques per 10 cm petri dish. The DNA probe was $P^{32}$ labeled double stranded oligonucleotide (17 mer) derived from the HIV-1 NRE-1 site (−173 to −156) upstream of the transcription initiation site. One positive plaque was found out of 45 plates screened, at a frequency of $2\times10^{-6}$. The positive plaque, named YC1A was then purified three times to obtain a 100% binding positive plaques (data not shown). The cDNA insert in YC1A, which is about 1300 base pairs, is from 170 to 1523 of SEQ ID NO:2, and was cloned into the EcoRI sites of cDNA1 (Invtrogen). The nucleotide sequence was determined using a sequencing kit purchases from USB (United States Biochemical). The first set of sequencing primers were the T7 and SP6 sequencing primers purchased from NEB (New England Biolabs). The additional sequencing primers were then determined and synthesized according to the sequences which resulted from the previous primers. The deduced amino acid sequence is that shown in SEQ ID NO:1 starting at the Met position 34 residue. See, FIG. 1A, the amino acids not part of the dotted underline. A secondary cDNA clone, YC1, was isolated by re-screening the library with a fragment of the cDNA from the clone YC1A as probe in DNA-DNA hybridization. The cDNA in YC1A was cloned into pMALc (NEB) and pcDNA1 (Invitrogen) to make pMAL-YC1A and pCD-YC1A, respectively, in the same orientation as it was in the original lambda phage vector. The plasmid pMAL-YC1A was used to transform *E. coli strain* TC1. The induction and the purification of the MBP-YC1 fusion protein and the subsequent separation of YC1 from MBP (maltose binding protein) was performed as taught in the procedure provided by the company (NEB). The cDNA from the clone YC1 was also cloned into pCDNA1, to make plasmid pCDYC1, in the orientation so that the expression of YC1 is driven by the CMV promoter. pMAL-YC1 was then constructed by cloning the cDNA from YC1 in frame with MBP in pMALc. The pMAL-YC1fs was made by partial digesting of pMALYC1 with the restriction endonuclease SalI and filling in the ends by the DNA polymerase I larger fragment and re-ligating. The fusion protein of MBP and the YC1 truncated in amino acid 79 was produced by transforming *E. coli* TG1 strain with pMAL-YC1fs.

Serine and threonine account for almost one-fifth of the total amino acids of this protein. This protein also contains a leucine zipper-like motif located near the center (amino acids 143–161) and two possible helix-turn helix in the center of the molecule (amino acids 112 to 164 and 187 to 226). FIG. 1A shows the amino acid sequence of the YC1, YC1A and YC1fs proteins.

The calculated molecular weight of the YC1 protein is 45 kD. The Leucine residues in the putative Leucine zipper is shown by the bold letters. The serine rich domain is indicated by the underline. The additional amino acids sequences derived from the secondary cDNA clone, resulting in the full length YC1 protein, is indicated by the dotted line. The truncated YC1 protein made from a frame shift mutation (YC1fs) is labeled by the arrow.

No significant sequence similarity was found with the deduced protein sequence of YC1A and proteins present in the NIH data base. An anti-serum to the protein encoded by YC1A was made and used to identify the protein in cellular lysates. The YC1A reading frame was fused to the maltose binding protein of *E. coli*. The fusion protein expressed in *E. coli* was purified by passage over a cross-link amalose column. Anti-sera to the YC1A protein was made by injecting mice with the YC1A protein cleaved from the fusion protein. The murine anti-sera recognizes the YC1A protein made with by the original phage and also recognizes the maltose binding YC1A fusion protein.

YC1A sequences were inserted into a eukaryotic expression vector under the control of the CMV promoter. The expression of endogenous in the endogenous YC1 protein from mammalian cells was then observed.

The bacterial proteins were labeled by adding 500 μci of $S^{35}$-Met (NEN) into 2 ml cultures of either YC1A infected Y1089 cells or pMAL-C11 transformed TG1 cells at the log-growth stage ($OD^{600}$=0.4), with or without IPTG to induce the Lac promoter. The cells were then incubated at 37° C. for 2 hours, followed by spinning-down the cells. To label the cultured mammalian cells, 500 μl $S^{35}$-Met was added to 5 ml cells, about $1 \times 10^6$ cells/ml, in the Met-minus medium with 10% FCS. 16 hours later, the cells were harvested by centrifugation at 1000 rpm for 5 minutes. In the case of labeling the exogenous YC1, 20 μg pCD-YC1A or pCD-YC1 were used to transfect $5 \times 10^6$ COS1 cells by the DEAE-Dextran method previously described [Lu, Y., et al, *J. Virol.* 64:5226 (1990)]. 32 hours post-transfection, 500 μl $S^{35}$-Met was added to the cultures to label the cellular proteins. The procedure of immunoprecipitation is that the bacterial pellet was resuspended in 1 ml RIPA buffer with 100 μg/ml lysozyme (Sigma) to lysis the cells. 300 μl supernatant of the cell lysate was then incubated with 1 μl mouse anti-YC1 serum, with or without 1 ug MBP-YC1 protein as the competitor, and 50 μl protein-A sepharose beads at 4° C. overnight. The beads were washed 5 times by RIPA buffer and then boiled in 50 μl protein loading buffer for 5 minutes. The samples were analyzed by a 12.5% SDS PAGE. The gel was then fixed, enhanced, and dried, followed by autoradiography.

Figure 2A:
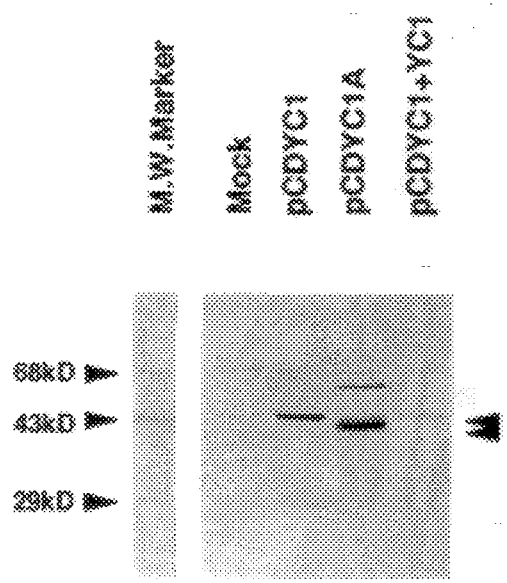
FIG. 2A shows a comparison of the authentic YC1 protein with the YC1 protein made from pCD-YC1A and pCD-YC1.
Figure 2B:
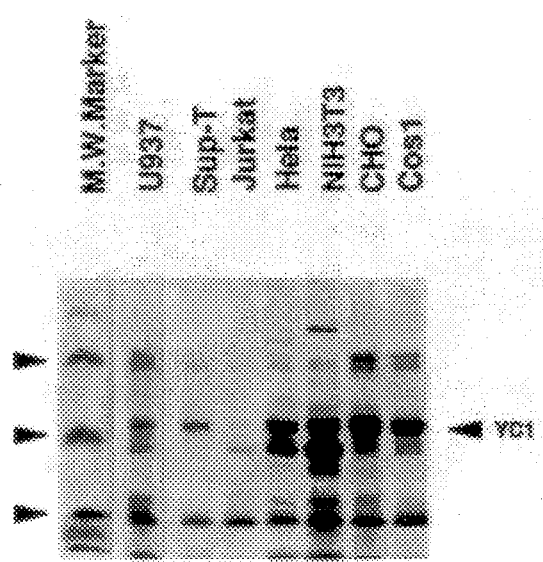
FIG. 2B shows the expression of the authentic YC1 protein in different mammalian cells.

FIGS. 2A–C shows the expression of endogenous and exogenous YC1 protein in mammalian cells. FIG. 2A shows that the mouse anti-YC1 serum recognizes YC1 protein produced by YC1 and pMAL-YC1. After the molecular weight markers, Line 1 is a mock-transfected cell; Lane 2 shows expression from pCDYC1, lane 3 shows expression from pCDYC1A, lane 4 compares the protein expressed from pCDYC1 and YC1 . However, it also shows that the metabolically-labelled cellular protein precipitated by the YC1A anti-serum migrates slightly more slowly on SDS polyacrylamtde gels than does that produced by YC1A. Thus, a new cDNA clone, YC1 , was isolated from the Jurkat cell library by rescreening with a 5'terminal DNA fragment of the YC1A clone. YC1 encodes a 406 amino acid long protein (SEQ ID NO:1) and includes an additional 23 amino terminal amino acids. As shown in FIG. 2A the size of the YC1 47 kD protein is indistinguishable from that of the authentic cellular protein. FIG. 2B shows that the mouse anti-YC1 serum recognizes the endogenous YC1 protein in mammalian cells. FIG. 2B, lane 1 is an MW marker. Lane 2 is a transfected U937 cell. Lane 3 is a transfected Sup-T cell. Lane 4 is a Jurkat cell. Lane 5 is a transfected HeLa cell. Lane 6 is an NIH-3T3 transfected cell. Lane 7 is a CHO cell. Lane 8 is a transfected COS 1 cell.

FIG. 2C shows the expression of endogenous YC1 protein in different mammalian cells. Lane 1 is the MW marker, lane 2 is a mock-transfected HeLa cell, Lane 3 is a transfected HeLa cell, Lane 4 is a mock-transfected Sup-T cell, Lane 5 is a transfected sup-T cell, Lane 6 is a transfected NIH-3T3 cell, Lane 7 is a mock-transfected NIH-3T3 cell, Lane 8 has a cell-type competitor.

Serine and threonine account for almost one-fifth of the total amino acids of the YC1 protein. This protein contains two motifs previously associated with DNA binding activity, a leucine zipper-like motif located near the center (amino acids 143 to 161) and two possible helix-turn-helix-turn-helix in the center of the molecule (amino acids 112 to 164 and 187 to 226). The ability of the protein made in bacteria to recognize a double stranded oligonucleotide corresponding to the NRE 1 sequence was determined. The fusion protein with the maltose binding protein of *E. coli* was purified and cleaved with factor Xa protease. The cleaved as well as uncleaved proteins preparations were resolved on an SDS containing polyacrylamide gel.

The procedure of using the affinity column to purify MBP fusion proteins is provided with the Kit purchased from New England Biolabs. In general, 2 mg fusion protein can be obtained from 1 liter of IPTG induced bacterial cultures. About 1 μg of each protein samples was loaded onto a 12.5% SDS polyacrylamide gel and the same loading pattern was duplicated on the same gel to prepare two identical filters for Western and Southwestern analysis. After the electrophoresis, the gel was blotted onto a nitrocellulose membrane and the efficiency of the transfer was controlled by the prestained molecular weightmarkers (BRL). The protocols of Western and Southwestern blot analysis were basically as described in Celenza, J. et al., *Science* 233:1175 (1986). In the Western analysis, the mouse anti-MBP-YC1 was diluted 1:5000. In the Southwestern analysis, $5 \times 10^6$ cpm of the $P^{32}$-labeled ds oligonucleotide derived from the HIV-1 USF site was used in a total of 5 ml binding buffer.

The conditions of the gel retardation analysis was as previously described (Lu, Y., et al., *J. Virol* 64, supra). The Hela cell nuclear extract was prepared by the Dignam procedure (Digham, et al., Nucleic Acids Res. 11, supra). 5 µg of the nuclear protein and 1×10⁶ cpm of the labeled HIV-1 NRE-1 oligonucleotide were used in the assay. The gel slice containing the DNA-protein complex was exposed to a UV source, UVGL-25, UVP, for 5 minutes at a distance of 5 cm. The protein was then eluted into solutions by incubating the smashed gels at room temperature overnight. One half of the protein sample was analyzed by SDS PAGE directly, and the other half was immuno-precipitated by the mouse anti-YC1 serum first, followed by SDS PAGE.

FIG. 3A shows Western blot analysis MBP-LacZ, MBP-YC1fs, MBP-YC1, MBP and YC1 using mouse anti-MBPYC1 serum.

In FIG. 3A; lane 1 is the MW MARKER, lane 2 MBP-LacZ, lane 3 MBP-YC1fs, lane 4, MBP-YC1, and lane 5 MBP, YC1.

FIG. 3B shows Southern blot analysis of the same sample using $P^{32}$-labelled DS oligonucleotide derived from the HIV-1 NRE-1 site as a probe.

FIG. 3C shows immunoprecipitation of HIV-1 NRE-1 binding protein from HeLa cell nuclear extract by YC1 anti-sera, which shows that the radioactive NRE-1 oligonucleotide binds both to the fusion protein and the 47 kD YC1 protein released from the fusion protein by proteolytic treatment. The probe did not bind to a fusion protein which contains a stop codon at a position corresponding to amino acid 108 of the YC1 protein (i.e. YC1fs). The radioactive oligonucleotide from the HIV-1 enhancer site (nucleotide −101 to −97) did not bind to the YC1 protein. The ability of the authentic cellular YC1 protein to bind the NRE-1 DNA was also examined. A slowly migrating complex between the radiolabelled NRE-1 DNA and a protein present in HeLa extracts was isolated from a non-denaturing polyacrylamtde gel.

The radioactive DNA probe was cross-linked by UV irradiation to proteins present in this slowly migrated complex by UV irradiation. The ability of YC1 anti-sera to precipitate proteins present in the DNA complex was determined. Lane 1 is MW. Marker, lane 2 HIV NRE-1-BP, lane 3 HIV NRE-1-BP and anti-YC1.

Figure 1A:
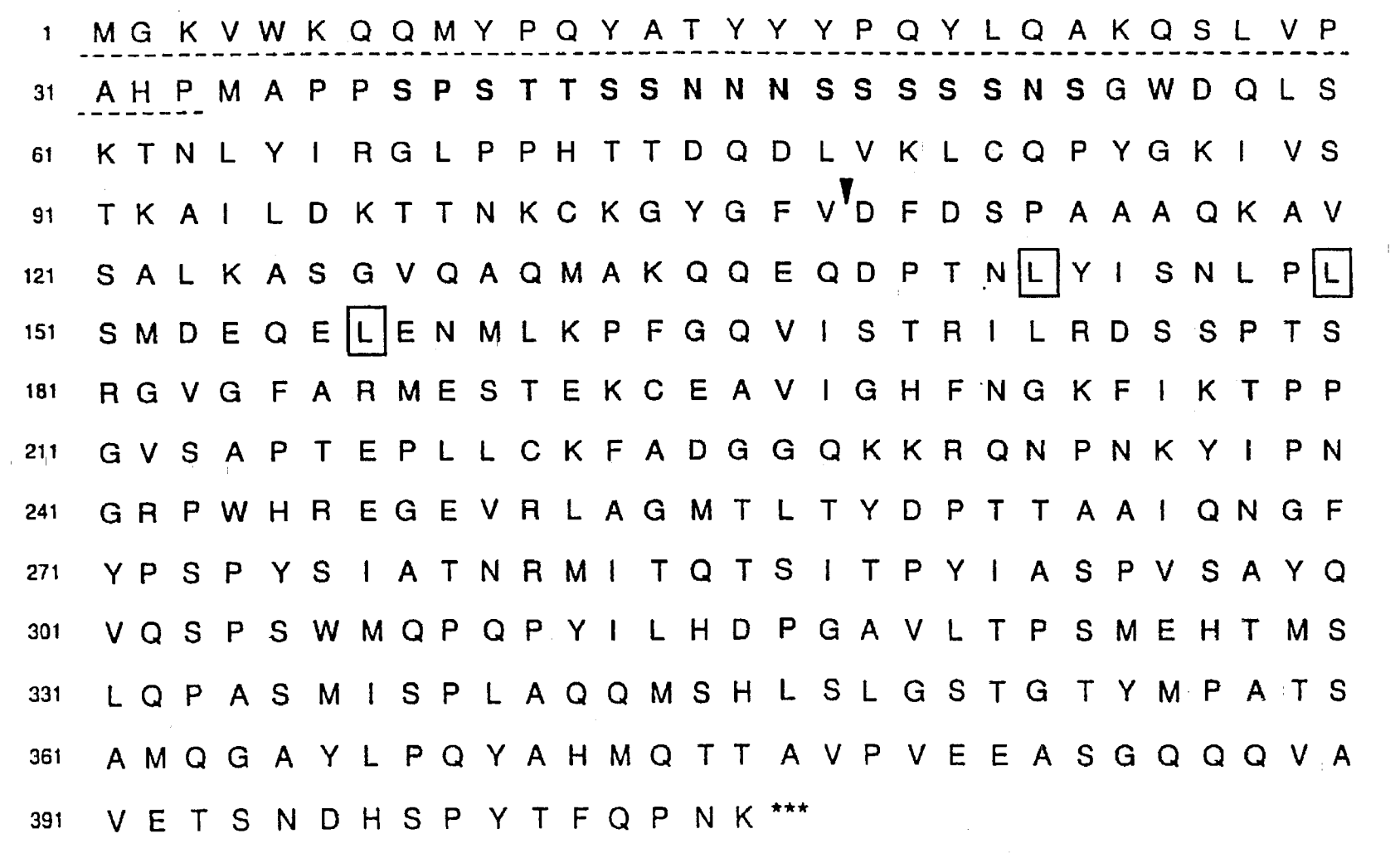

FIG. 1B shows a Southern Blot analysis of the YC1 protein. Human genomic DNA from Jurkat cells (lanes 1 and 2) and mouse genomic liver DNA (lanes 3 and 4) was ECOR1 (lanes 1 and 3) or BamH1 (lanes 2 and 4) digested. After size separation the DNA was blotted to Gene Screen Plus filters (Dupont) and hybridized. A PCR generated fragment spanning YC1 amino acids 303-392 was labelled by random priming and used as a probe.

A protein having similar electrophoretic mobility to YC1 is labelled by the radioactive NRE-1 and recognized by the YC1 anti-sera. The YC1 protein also appears to bind RNA tightly and non-specifically. The absorbance spectrum of the 47 kD (280/260 equals 0.6). YC1 protein purified for bacteria after cleavage from the maltose binding protein suggests that it contains substantial amounts of nucleic acid. Short RNA fragment, 10 to 25 nucleotides long, can be visualized by ethidiumbromide staining of an agarose gel. These fragments are sensitive to RNAse but not to DNAse treatment.

Figure 1C:
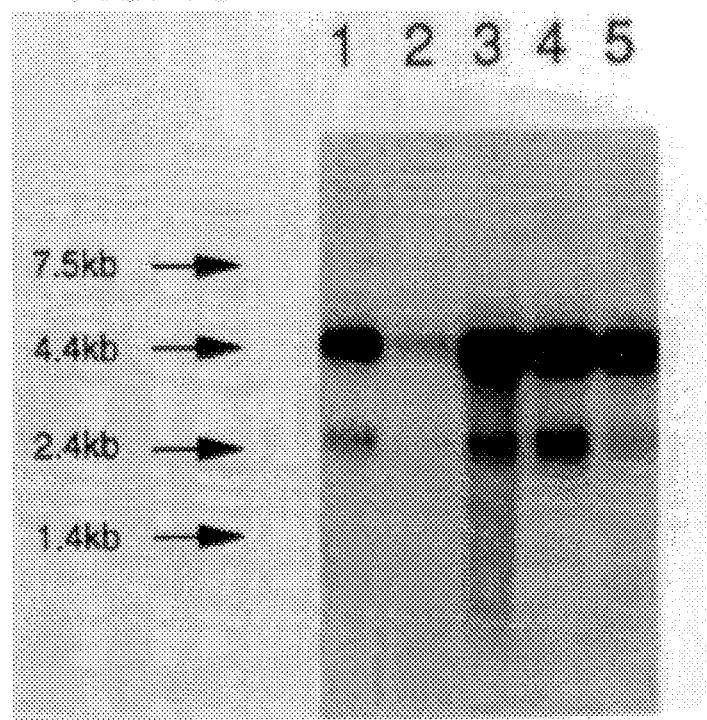
FIGS. 1C and D show YC1 Norther blot analyses of YC1.
Figure 1D:
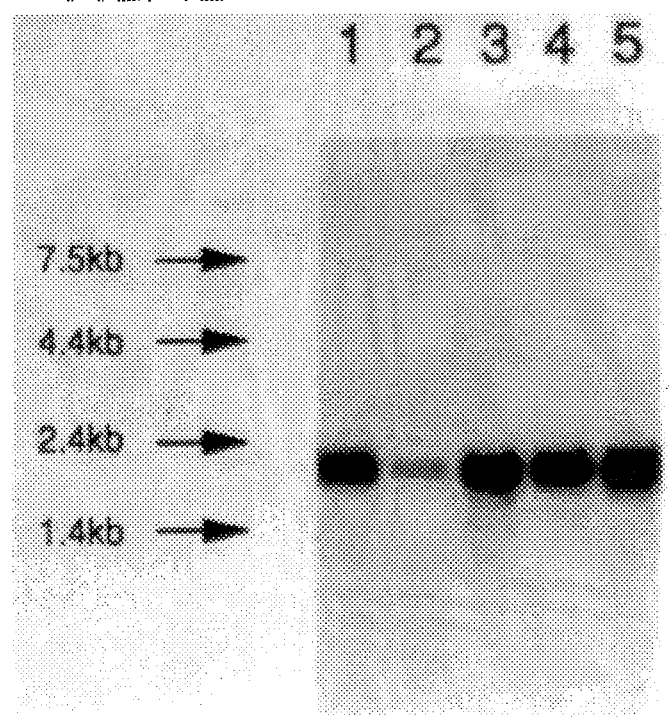
FIG. 1A shows the amino acid sequence of YC1 with various domains labeled.
FIGS. 1E is a partial sequence comparison of HIV-1/NRE-1 (SEQ ID NO:4), IL-2Rα (SEQ ID NO:3) and the USF binding site (SEQ ID NO:5) in Adenovirus 2 major late promoters

As shown in FIGS. 1C and 1D, mRNA was isolated from Jurkat (lane 1), SupT1 (lane 2) U937 (lane 3), HeLa (lane 4) or COS (lane 5) cells using the Fast Track mRNA purification kit (Invitrogen), size separated on formaldehyde containing agarose gels and transferred to a Gene Screen Plus Filter. The filter was first hybridized to a PCR generated probe spanning YC1 amino acids 37-39 (FIG. 1C) and then to a beta actin probe (FIG. 1D). Both probes were labelled by random priming.

FIG. 1E shows a show a sequence comparison of HIV-1 NRE-1 (SEQ DI NO:4), IL-2Rα promoter (SEQ ID NO:3), and binding site in Adenovirus 2 major date promoter SEQ ID NO:5).

The YC1 protein is expressed in many human cell lines. A 47 kD protein was precipitated from the human epithelial cell lines, HeLa, the CD4+ T-cell line, SupT1 and Jurkat, and the human promylocytic cell line, U937, (FIG. 2B). The binding of the anti-sera to the 47 kD protein was specifically decreased by adding bacterially-produced YC1 protein (FIG. 2C). YC1 anti-sera also recognizes a 47 kD protein expressed in non-human cell lines, including the monkey cell line COS, the murine cell line, NIH3T3, and the hamster cell line, CHO (FIG. 2B). Southern blot analysis of mouse in human genomic DNA was performed with a PCR generated probe spanning amino acids 303-392 of the YC1 protein. A single band in EGO R1 digested mouse genomic DNA indicates that YC1 is present as a single copy gene in the mouse genome. The human genome appears to harbor more than one gene (FIG. 1B). This was confirmed by isolated lambda-phage clones from a genomic library using the same probe as in the Southern blot.

Partial sequence analysis revealed two genes, one with and one without introns. The intronless gene is assumed to be a pseudogene that arose after divergence of the mouse and human species. Northern blot analysis was performed on mRNA isolated from human leukocyte cell lines, as well as human epithelial carcinoma and a monkey fibroblast cell line. All show a strong 4.5 kB band and a weaker 2.5 kB band (FIG. 2C). Rehybridizing the same filter with a beta actin probe revealed that the level of YC1 transcripts was similar in all cell lines (FIG. 2D). Detection of YC1 transcripts in mouse liver mRNA probes confirmed that YC1 is expressed in a variety of different tissues. The purified YC1 proteins activity was determined in HeLa cells in an in vitro transcription assay using the HIV-1 LTR.

The procedure of the in vitro transcription analysis is essentially the same as the one described by J. Manley, Transcription and Translation:A Practical Approach, Edited by B. D. Hames & S. J. Higgins, IRL Press, pp. 71 (1984), except for the following changes. 40 µg protein of HeLa cell nuclear extract, instead of the whole cell extract, was used for each reaction. 4 µg of plasmid DNA, digested once at the NcoI site in the CAT gene, was used as the DNA template. The HIV-1 LTR-CAT, HIV-1 LTR DUSF, TK-CAT, IL-2-CAT, and IL-2R CAT plasmids were digested by restriction endonculease Nco 1 which cut once in the CAT gene. The MBP-LacZ, MBP-YC1fs, and MBP-YC1 used in the assay were purified by a modified protocol. It is observed that the amylose column purified MBP-YC1 protein binds to a significant amount of bacterial RNA, while MBP-YC1fs does not. Therefore, the supernatant of the bacterial cell lysate containing MBP-YC1 protein was treated by RNase A at the concentration of 1 ng/ml at room temperature for 20 minutes. The lysate, in a final volume of 15 ml, was then loaded onto the amylose column. The column was then washed by a total of 500 ml the column buffer to remove the RNase. As the controls, the MBP-LacA and MBP-YC1fs were also treated with the RNase and purified under the same conditions. In each assays, MBP-YC1fs served as the negative control for the YC1 activity. The possibility that the purified protein still contains RNase activity was excluded by the fact that YC1 has no effect on the IL-2 and the TK promoters. In addition, the RNAse treated MBP-YC1fs serves as the controls for each assays.

Figure 4:
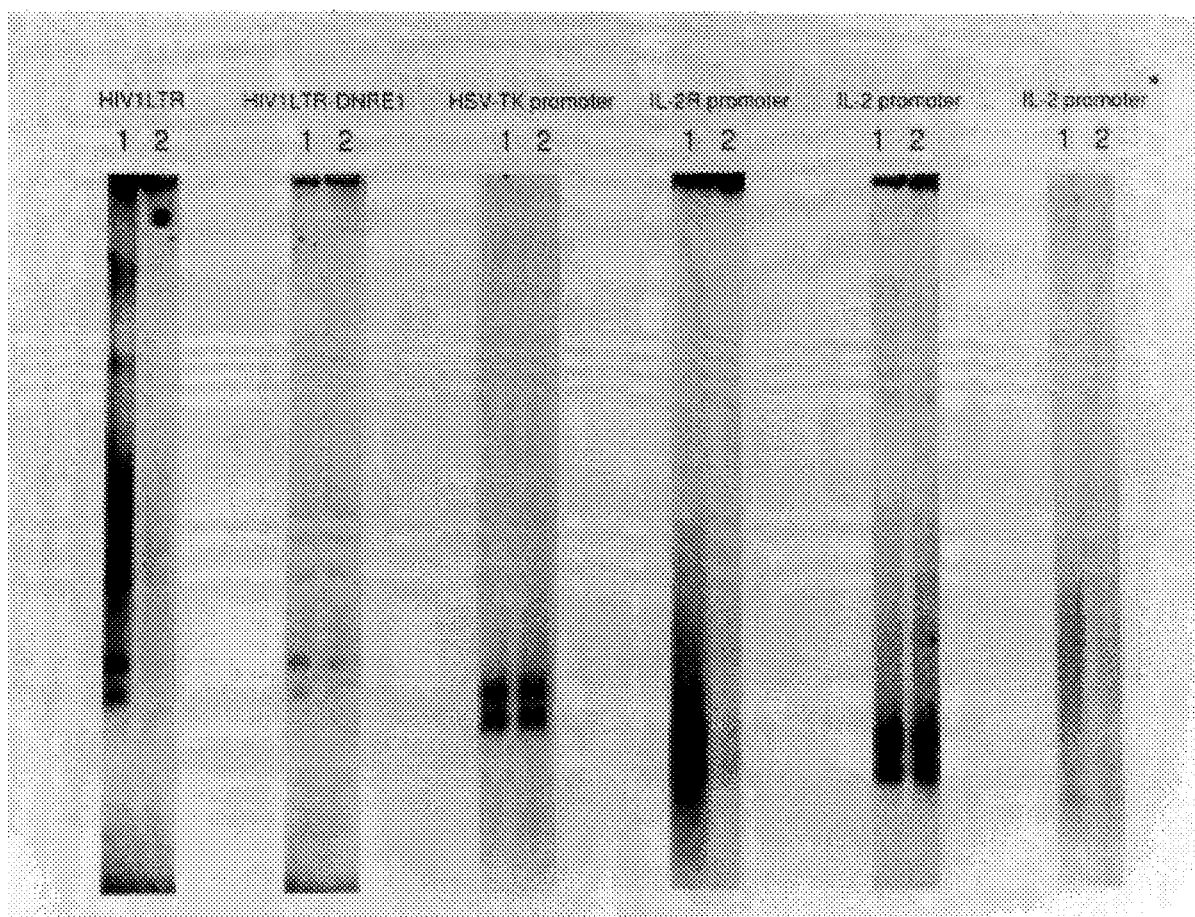
FIG. 4 shows a functional analysis of YC1 protein in an in vitro transcription system.

FIG. 4 shows a functional analysis of YC1 protein in an in vitro transcription system. It shows the repression of HIV-1 LTR directed transcription by YC1 protein and the promoter specificity of YC1 activity. The addition of the purified 47 kD YC1 protein eliminates detectable RNA synthesis directed by the HIV-1 LTR (first two columns). The YC1 protein does not reduce the amount of RNA made by the HIV-1 LTR promoter deleted for the NRE-1 binding site (second two columns). See, FIG. 4. Similar experiments were also performed using the Interleukin-2 receptor alpha (IL-2Rα) (fourth two columns) and Interleukin-2 (IL-2) (last columns) and herpes simplex thymidine kinase (TK) promoters (third two columns). The data of FIG. 4 shows that the YC1 protein also inhibits RNA transcription directed by the IL-2R α-promoter but not by the IL-2 and herpes simplex TK promoters. In FIG. 4 the two lanes show expression with addition of YC1fs (lanes 1) and with addition of YC1 (lanes 2). It was previously noted that a sequence in the negative regulatory sequence located distal to the IL-2R a-promoter is identical to the RNA1 sequence. Lu, Y., et al. Genetic Structure and Regulation of HIV, Edited by W. A., Haseltine and F. Wong-Stahl, Raven Press, pg. 415–435 (1991); Smith, M. R., et al. *Proc. Natl. Acad. Sci. USA* 86:8526–8520 (1989). The above data shows that the YC1 protein will bind to the NRE-1 sequence and will repress transcription of both the HIV-1 and IL-2 Rα-promoters. Since the YC1 protein binds to a sequence which has been previously recognized as being associated with the repression of HIV-1 LTR and IL-2 Rα, we expect that the YC1 protein is a constitutive repressor of transcription of genes that contain this sequence and by adding this sequence to a gene once can negatively regulate any gene of interest. The NRE-1 binding sequence is similar to the USF-1 sequence initially described as a regulatory element present in the adenovirus E1A promoter. However, the YC1 protein is not similar in sequence to the cellular protein that binds the USF-1, the USF-1 binding protein [Gregor, P., et al., Gene Y. Development For:1730–1740 (1990)]. This USF-1 binding protein has previously been shown to bind to the NRE-1 sequence of the HIV LTR. However, the addition of the USF-1 binding protein to the in vitro extracts does not repress transcription directed by the HIV-1 LTR. Thus, it is clear that the USF-1 binding protein and the YC1 protein perform different functions.

In contrast, the HIV-1 and IL-2 Rα are coordinately regulated. Both promoters are inactivated in arresting primary T-cells and are activated by signals that stimulate T-cell proliferation. The HIV-1 LTR and IL-2 Rα-promoters both contain NF-κB binding sites. The IL-2 Rα and HIV-1 LTR are both activated by binding of the P65-P50NF-178 complex to the promoter. The regulation of these two gene promoters can be extended to include repression of expression via the protein YC1. The fact that YC1 RNA and protein expression, as well as NRE-1 binding activity is constitutive whereas expression of the NF-KBP65-P50 complex is induced, indicates that activation of the HIV-1 LTR and IL-2 Rα-promoters by NF-KB is dominant to repression of those promoters by YC1. This suggests a dual action of cellular repressors and activators in gene expression.

It is evident that those skilled in the art given the benefit of the foregoing disclosure may make numerous other uses and modifications thereof and departures from the specific embodiments described herein without departing from the inventive concepts, and the present invention is to be limited solely by the scope and spirit of the appended claims.

We claim:

1. An isolated and purified nucleic acid segment having SEQ ID NO:2 or a portion of said segment wherein said segment or said portion thereof encodes a protein that binds to a HIV LTR NRE-1 site and inhibits expression of a gene operably linked to said HIV LTR NRE-1 site.

2. An RNA molecule encoded by the nucleic acid segment in claim 1.

3. A vector comprising a promoter operably linked to the nucleic acid segment of claim 1.

4. An isolated and purified nucleic acid sequence having a segment having SEQ ID NO:2 or a portion of said segment, wherein said segment or said portion encodes a protein that binds to a HIV LTR NRE-1 site and inhibits expression of a gene operably linked to said HIV LTR NRE-1 site, wherein said segment or said portion is operably linked to a promoter.

* * * * *

UNITED STATES PATENT AND TRADEMARK OFFICE
CERTIFICATE OF CORRECTION

PATENT NO. : 5,652,144
DATED : July 29, 1997
INVENTOR(S) : Yichen Lu, William A. Haseltine It is certified that error appears in the above-identified patent and that said Letters Patent is hereby corrected as shown below:

Col. 1, before line 4, insert -- -The above invention was made, in part, with support from NIH Grant No. AI24845 and the United States Government has certain rights thereto.- -

Signed and Sealed this

Tenth Day of August, 1999

*Attest:*

*Attesting Officer*

Q. TODD DICKINSON

*Acting Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 406 amino acids
( B ) TYPE: amino acid
( C ) STRANDEDNESS: unknown
( D ) TOPOLOGY: unknown ( x i ) SEQUENCE DESCRIPTION: SEQ ID NO:1:

| Met | Gly | Lys | Val | Trp | Lys | Gln | Gln | Met | Tyr | Pro | Gln | Tyr | Ala | Thr | Tyr |
|---|---|---|---|---|---|---|---|---|---|---|---|---|---|---|---|
| 1 | | | | 5 | | | | | 10 | | | | | 15 | |

| Tyr | Tyr | Pro | Gln | Tyr | Leu | Gln | Ala | Lys | Gln | Ser | Leu | Val | Pro | Ala | His |
|---|---|---|---|---|---|---|---|---|---|---|---|---|---|---|---|
| | | | 20 | | | | | 25 | | | | | 30 | | |

| Pro | Met | Ala | Pro | Pro | Ser | Pro | Ser | Thr | Thr | Ser | Ser | Asn | Asn | Asn | Ser |
|---|---|---|---|---|---|---|---|---|---|---|---|---|---|---|---|
| | | 35 | | | | | 40 | | | | | 45 | | | |

| Ser | Ser | Ser | Ser | Asn | Ser | Gly | Trp | Asp | Gln | Leu | Ser | Asn | Ala | Asn | Leu |
|---|---|---|---|---|---|---|---|---|---|---|---|---|---|---|---|
| | 50 | | | | | 55 | | | | | 60 | | | | |

| Tyr | Ile | Arg | Gly | Leu | Pro | Pro | His | Thr | Thr | Asp | Gln | Asp | Leu | Val | Lys |
|---|---|---|---|---|---|---|---|---|---|---|---|---|---|---|---|
| 65 | | | | | 70 | | | | | 75 | | | | | 80 |

| Leu | Cys | Gln | Pro | Tyr | Gly | Lys | Ile | Val | Ser | Thr | Lys | Ala | Ile | Leu | Asp |
|---|---|---|---|---|---|---|---|---|---|---|---|---|---|---|---|
| | | | | 85 | | | | | 90 | | | | | 95 | |

| Lys | Thr | Thr | Asn | Lys | Cys | Lys | Gly | Tyr | Gly | Phe | Val | Asp | Phe | Asp | Ser |
|---|---|---|---|---|---|---|---|---|---|---|---|---|---|---|---|
| | | | 100 | | | | | 105 | | | | | 110 | | |

| | | | | | | | | | | | | | | |
|---|---|---|---|---|---|---|---|---|---|---|---|---|---|---|
|Pro|Ala|Ala|Ala<br>115|Gln|Lys|Ala|Val<br>120|Ser|Ala|Leu|Lys<br>125|Ala|Ser|Gly|Val|
|Gln|Ala<br>130|Gln|Met|Ala|Lys<br>135|Gln|Gln|Glu|Gln<br>140|Asp|Pro|Thr|Asn|Leu|Tyr|
|Ile<br>145|Ser|Asn|Leu|Pro|Leu<br>150|Ser|Met|Asp|Glu<br>155|Gln|Leu|Glu|Asn|Met<br>160|
|Leu|Lys|Pro|Phe|Gly<br>165|Gln|Val|Ile|Ser|Thr<br>170|Arg|Ile|Leu|Arg|Asp<br>175|Ser|
|Ser|Pro|Thr|Ser<br>180|Arg|Gly|Val|Gly|Phe<br>185|Ala|Arg|Met|Glu|Ser<br>190|Thr|Glu|
|Lys|Cys|Glu<br>195|Ala|Val|Ile|Gly|His<br>200|Phe|Asn|Gly|Lys|Phe<br>205|Ile|Lys|Thr|
|Pro|Pro<br>210|Gly|Val|Ser|Ala|Pro<br>215|Thr|Glu|Pro|Leu|Leu<br>220|Cys|Lys|Phe|Ala|
|Asp<br>225|Gly|Gly|Gln|Lys|Lys<br>230|Arg|Gln|Asn|Pro|Asn<br>235|Lys|Tyr|Ile|Pro|Asn<br>240|
|Gly|Arg|Pro|Trp|His<br>245|Arg|Glu|Gly|Glu|Val<br>250|Arg|Leu|Ala|Gly|Met<br>255|Thr|
|Leu|Thr|Tyr|Asp<br>260|Pro|Thr|Thr|Ala|Ala<br>265|Ile|Gln|Asn|Gly|Phe<br>270|Tyr|Pro|
|Ser|Pro|Tyr<br>275|Ser|Ile|Ala|Thr|Asn<br>280|Arg|Met|Ile|Thr|Gln<br>285|Thr|Ser|Ile|
|Thr|Pro<br>290|Tyr|Ile|Ala|Ser|Pro<br>295|Val|Ser|Ala|Tyr|Gln<br>300|Val|Gln|Ser|Pro|
|Ser<br>305|Trp|Met|Gln|Pro|Gln<br>310|Pro|Tyr|Ile|Leu|His<br>315|Asp|Pro|Gly|Ala|Val<br>320|
|Leu|Thr|Pro|Ser|Met<br>325|Glu|His|Thr|Met|Ser<br>330|Leu|Gln|Pro|Ala|Ser<br>335|Met|
|Ile|Ser|Pro|Leu<br>340|Ala|Gln|Gln|Met|Ser<br>345|His|Leu|Ser|Leu|Gly<br>350|Ser|Thr|
|Gly|Thr|Tyr|Met<br>355|Pro|Ala|Thr|Ser|Ala<br>360|Met|Gln|Gly|Ala|Tyr<br>365|Leu|Pro|
|Gln|Tyr|Ala<br>370|His|Met|Gln|Thr|Thr<br>375|Ala|Val|Pro|Val|Glu<br>380|Glu|Ala|Ser|
|Gly<br>385|Gln|Gln|Gln|Val|Ala<br>390|Val|Glu|Thr|Ser|Asn<br>395|Asp|His|Ser|Pro|Tyr<br>400|
|Thr|Phe|Gln|Pro|Asn<br>405|Lys|

( 2 ) INFORMATION FOR SEQ ID NO:2:

( i ) SEQUENCE CHARACTERISTICS:
        ( A ) LENGTH: 1534 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:2:

```
GAATTCGGGC CGAGACTTGG AAACCCCAAA GTGTCCGCGA CCCTGCACGG CAGCTCCCTT      60
CCAGCTTCAT GGGCAAAGTG TGGAAACAGC AGATGTACCC TCAGTACGCC ACCTACTATT     120
ACCCCCAGTA TCTGCAAGCC AAGCAGTCTC TGGTCCCAGC CCACCCCATG GCCCCTCCCA     180
GTCCCAGCAC CACCAGCAGT AATAACAACA GTAGCAGCAG TAGCAACTCA GGATGGGATC     240
AGCTCAGCAA AACGAACCTC TATATCCGAG GACTGCCTCC CCACACCACC GACCAGGACC     300
TGGTGAAGCT CTGTCAACCA TATGGGAAAA TAGTCTCCAC AAAGGCAATT TTGGATAAGA     360
```

```
CAACGAACAA ATGCAAAGGT TATGGTTTTG TCGACTTTGA CAGCCCTGCA GCAGCTCAAA      420
AAGCTGTGTC TGCCCTGAAG GCCAGTGGGG TTCAAGCTCA AATGGCAAAG CAACAGGAAC      480
AAGATCCTAC CAACCTCTAC ATTTCTAATT TGCCACTCTC CATGGATGAG CAAGAACTAG      540
AAAATATGCT CAAACCATTT GGACAAGTTA TTTCTACAAG GATACTACGT GATTCCAGTC      600
CTACAAGTCG TGGTGTTGGC TTTGCTAGGA TGGAATCAAC AGAAAAATGT GAAGCTGTTA      660
TTGGTCATTT TAATGGAAAA TTTATTAAGA CACCACCAGG AGTTTCTGCC CCCACAGAAC      720
CTTTATTGTG TAAGTTTGCT GATGGAGGAC AGAAAAAGAG ACAGAACCCA AACAAATACA      780
TCCCTAATGG AAGACCATGG CATAGAGAAG GAGAGGTGAG ACTTGCTGGA ATGACACTTA      840
CTTACGACCC AACTACAGCT GCTATACAGA ACGGATTTTA TCCTTCACCA TACAGTATTG      900
CTACAAACCG AATGATCACT CAAACTTCTA TTACACCCTA TATTGCATCT CCTGTATCTG      960
CCTACCAGGT GCAAAGTCCT TCGTGGATGC AACCTCAACC ATATATTCTA CACGACCCTG     1020
GTGCCGTGTT AACTCCCTCA ATGGAGCACA CCATGTCACT ACAGCCCGCA TCAATGATCA     1080
GCCCTCTGGC CCAGCAGATG AGTCATCTGT CACTAGGCAG CACCGGAACA TACATGCCTG     1140
CAACGTCAGC TATGCAAGGA GCCTACTTGC CACAGTATGC ACATATGCAG ACGACAGCGG     1200
TTCCTGTTGA GGAGGCAAGT GGTCAACAGC AGGTGGCTGT CGAGACGTCT AATGACCATT     1260
CTCCATATAC CTTTCAACCT AATAAGTAAC TGTGAGATGT ACAGAAAGGT GTTCTTACAT     1320
GAAGAAGGGT GTGAAGGCTG AACAATCATG GATTTTCTG ATCAATTGTG CTTTAGGAAA      1380
TTATTGACAG TTTTGCACAG GTTCTTGAAA ACGTTATTTA TAATGAAATC AACTAAAACT     1440
ATTTTTGCTA TAAGTTCTAT AAGGTGCATA AAACCCTTAA ATTCATCTAG TAGCTGTTCC     1500
CCCGAACAGG TTTATTTTAG TAAAAAAAAA AAAA                                 1534
```

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: unknown
        (D) TOPOLOGY: unknown (xi) SEQUENCE DESCRIPTION: SEQ ID NO:3:

```
GGCCACGTGA CC                                                           12
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (xi) SEQUENCE DESCRIPTION: SEQ ID NO:4:

```
AGCATTTCAT CACTGGC                                                      17
```

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (xi) SEQUENCE DESCRIPTION: SEQ ID NO:5:

```
TTCATCCCAG G                                                            11
```